(12) United States Patent
Mentzelopoulos et al.

(10) Patent No.: US 6,251,069 B1
(45) Date of Patent: Jun. 26, 2001

(54) LARYNGOSCOPE WITH A FLEXIBLE BLADE

(76) Inventors: Spyros Mentzelopoulos, 2A Kipseli Street, GR-113 62, Athens (GR); Constantinos Balas, 12 Zacharioudaki Street, GR-713 05, Iraklion (GR)

( * ) Notice: Subject to any disclaimer, the term of this patent is extended or adjusted under 35 U.S.C. 154(b) by 0 days.

(21) Appl. No.: 09/254,772

(22) PCT Filed: Nov. 5, 1997

(86) PCT No.: PCT/GR97/00038

§ 371 Date: Mar. 9, 1999

§ 102(e) Date: Mar. 9, 1999

(87) PCT Pub. No.: WO98/19589

PCT Pub. Date: May 14, 1998

(30) Foreign Application Priority Data

Nov. 7, 1996 (GR) .............................................. 960100378

(51) Int. Cl.⁷ .................................................. A61B 1/267
(52) U.S. Cl. ........................ 600/196; 600/190; 600/185; 600/146
(58) Field of Search .................................... 600/190, 196, 600/187, 185, 146, 116

(56) References Cited

U.S. PATENT DOCUMENTS

| | | |
|---|---|---|
| 3,856,001 | 12/1974 | Phillips . |
| 4,086,919 | 5/1978 | Bullard . |
| 4,306,547 | 12/1981 | Lowell . |
| 4,329,983 | 5/1982 | Fletcher . |
| 4,384,570 * | 5/1983 | Roberts ...................................... 128/4 |
| 4,573,451 * | 3/1986 | Bauman ................................... 128/11 |
| 4,574,784 * | 3/1986 | Soloway .................................. 128/11 |
| 4,681,094 * | 7/1987 | Rolnick ................................... 128/10 |
| 4,793,327 | 12/1988 | Frankel . |
| 4,982,729 | 1/1991 | Wu . |
| 5,003,962 | 4/1991 | Choi . |
| 5,016,614 | 5/1991 | Mac Allister . |
| 5,038,766 | 8/1991 | Parker . |
| 5,203,320 | 4/1993 | Augustine . |
| 5,431,152 | 7/1995 | Flam et al. . |

* cited by examiner

*Primary Examiner*—Lee Cohen
*Assistant Examiner*—Jocelyn Ram
(74) *Attorney, Agent, or Firm*—Herbert Dubno

(57) ABSTRACT

A laryngoscope having a flexible blade which is hinged and having in the handle articulation control for the hinged portion of the blade as well as an actuator for a pair of balloons on the blade connected with double-lumen tubes.

25 Claims, 6 Drawing Sheets

LARYNGOSCOPE WITH A FLEXIBLE BLADE

CROSS REFERENCE TO RELATED APPLICATIONS

This application is a national stage of PCT/GR97/00038 filed Nov. 5, 1997 and based on Greek national application 960100398 filed Nov. 7, 1996 under the International Convention.

FIELD OF THE INVENTION

This invention generally relates to examining or viewing devices and techniques used in the management of the upper airway.

BRIEF DESCRIPTION OF THE PRIOR ART

Endotracheal intubation is a medical procedure, that secures a patient's airway through placement of a tube in the patient's trachea in order to facilitate either spontaneous or controlled gas exchange.

Endotracheal intubation is routinely carried out in operating rooms after induction of anesthesia or in emergencies, and is usually achieved without great difficulty under direct vision provided by a laryngoscope.

The laryngoscope is a medical instrument used to expose the patient's vocal cords which narrow the uppermost end the trachea, i.e. the larynx.

Direct laryngoscopy is usually performed with a laryngoscope having a rigid straight blade (known as a Miller type blade), or a rigid curved blade (known as a Macintosh type blade). The most commonly used technique consists of the following steps:

(i) Flexion of the patient's neck and extension of his (or her) head in order to achieve alignment of the oral, pharyngeal and laryngeal axis, (ii) Opening of the patient's mouth and introduction of the rigid blade into the right side of the oropharynx with care to avoid the teeth, (iii) Displacement of the tongue to the left and up into the foot of the pharynx by the blade's flange, (iv) Insertion of the tip of the blade into the vallecula, (v) Elevation of the handle up and away from the patient in a plane perpendicular in his (or her) mandible and exposure of the vocal cords, (vi) Insertion of the endotracheal tube through the exposed vocal cords.

However it is sometimes impossible to view the larynx by using the "traditional" direct laryngoscopy even in a patient with no (or very subtle) physical signs of difficult upper airway management.

Conditions associated with a difficult endotracheal intubation include obesity trauma (laryngeal fracture, mandibular or maxillary fracture, inhalation burn, cervical spine injury, temporomandibular joint dislocation), inadequate neck extension (rheumatoid arthritis, ankylosing spondylitis, halo traction), anatomic variations (micrognathia, prognathism, large tongue, arched palate, short neck prominent upper incisors), presence of a foreign body in the upper airway congenital anomalies (Pierre-Robin's syndrome, Treacher Collins' syndrome, laryngeal atresia, Goldenhar's syndrome, craniofacial dysostosis), infections (submandibular abscess, peritonsilar abscess, epiglottitis) and tumors (cystic hygroma, hemangioma, hematoma).

Patients with a potentially difficult intubation are frequently intubated awake and through the nose blindly or via fiberoptic endoscopy in order to maintain the protective reflexes against aspiration until the upper airway is secured.

The fiberoptic bronchoscope is a tubular instrument which utilizes flexible fiberoptic bundles to transmit light and visual images during examination of the upper and lower airways. It also contains one longitudinal channel extending from the rearward end to the tip through which oxygen can be insufflated and suction can be applied, and a lever at the proximal end to manoeuvre its tip.

There are several instruments and alternative techniques used in order to facilitate the management of the difficult airway.

Some of the instruments that can be used for laryngoscopy and endotracheal intubation are disclosed by the following patents:

1. Phillips, U.S. Pat. No. 3,856,001 discloses a rigid laryngoscope blade with a straight and a curved portion containing a longitudinal channel which forms an endotracheal tube passage. A light source is secured on one side of the blade (at the forward end of the straight portion) and aimed inwardly and downwardly. The light source is connected via electrical wires to a power source located in the handle.

2. Bullard, U.S. Pat. No. 4,086,919 discloses a rigid fiberoptic laryngoscope having a curved blade with a proximal connection member for connection to a laryngoscope handle and an eyepiece extending outwardly from the blade's proximal end. Fiberoptic bundles extend along the longitudinal axis of the blade up to the blade's distal end. An endotracheal tube can be passed alongside the fiberoptic bundle into the larynx and trachea.

3. Lowell, U.S. Pat. No. 4,306,547 discloses a rigid fiberoptic laryngoscope with a forwardly extended blade and a tube supporting channel. Fiberoptic bundles extend longitudinally along the top wall and terminate at the distal end of the channel. These bundles are proximally connected to a light source and a viewing assembly.

4. Fletcher, U.S. Pat. No. 4,329,983 discloses a guide instrument for endotracheal tubes which consists of a flexible bar that is inserted into the endotracheal tube and a flexible line extending along the bar which can be manipulated to flex the bar in a "bowed fashion" against the endotracheal tube so that the tube can be urged forwardly toward the trachea and away from the esophagus. This device can be used along with direct laryngoscopy in order to intubate an anteriorly located larynx.

5. Roberts, U.S. Pat. No. 4,384,570 discloses a rigid laryngoscope comprising an elongated blade shaped to fit into the oral pharynx of a patient and a handle consisting of a rigid section attached to one end of the blade, a movable section attached to the handle's rigid section and adapted to pivot about an axis being both substantially perpendicular to the length of the rigid handle section and extending in substantially the same direction as the length of the blade and means for locking the movable handle section during laryngoscopy. The use of this laryngoscope may decrease the risk of upper airway trauma when compared with the traditional laryngoscopic technique.

6. Baumann, U.S. Pat. No. 4,573,451 discloses a rigid laryngoscope blade with a bendable tip which can be actuated by operable means preferably located at the proximal end of the blade. This blade can be suitable to patients in which the traditional laryngoscopic procedures do not adequately expose the patient's larynx.

7. Frankel, U.S. Pat. No. 4,793,327 discloses a blind intubation instrument, which has an airway opening device, which is inserted into the patient's mouth and adjusted to a fixed position to hold the mouth open while an automated intubation guide is inserted for guiding an endotracheal tube into the trachea. The guide is fed into the mouth through an opening of the airway opening device, through which an endotracheal tube is fed into the mouth as well. The guide also has an adaptor or track which allows blind manipulation of the distal part of the endotracheal tube in order to achieve its insertion into the trachea after which the guide is withdrawn and the airway opening device removed from the mouth.

8. Wu, U.S. Pat. No. 4,982,729 discloses a rigid fiberoptic laryngoscope having an integral handle and a curved blade with fiberoptic bundles extending longitudinally along the blade and terminating at its tip. A releasably attachable (to the blade) bivalve element forms a passage for threading an endotracheal tube through the distal part of the blade.

9. Choi, U.S. Pat. No. 5,003,962 discloses an improved double angle blade or spatula which has three segments lengthwise. The proximal end of the blade is coupled so that it extends outward "L-fashion" from the end of the handle. The blade is then bent inwardly through a first and second bend toward the principal axis of the handle forming two acute angles of 20 and 30 degrees at the first and second bend respectively. The first bend is formed on the blade at about halfway between its proximal end and its tip and the second bend is formed at the distal third of the distal half of the blade. The principal object of this modified blade is to improve the difficult airway management.

10. Mac Allister, U.S. Pat. No. 5,016,614 discloses an endotracheal intubation instrument with a handle and a mechanism for retaining an endotracheal tube on an elongated obturator element extending from the handle and releasing the endotracheal tube therefrom. The obturator device includes an endoscope which permits visualization.

11. Parker, U.S. Pat. No. 5,038,766 discloses a disposable one-piece, contoured guide element with a channel which is releasably mounted at the end of a curved blade and handle. The device is used for blindly guiding and aiming orolaryngeal and oroesophageal tubular members.

12. Augustine, U.S. Pat. No. 5,203,320 discloses a rigid contoured fiberoptic tracheal intubation guide having a through bore for holding an endotracheal tube. Correct positioning of the device is detected by external palpitation of the neck of the patient and tracheal intubation is confirmed with fiberoptic visualization.

13. Flam and Gilbert, U.S. Pat. No. 5,431,152 discloses an oral fiberoptic intubating apparatus and method. This instrument has an elongate curvilinear blade member releasably attachable to a handle and a central channel sized to removably receive and slidably engage an endotracheal tube therein, an elongate tubular housing removably connected at its forward end to the rearward end of the endotracheal tube which removably receives a fiberoptic scope having an eyepiece at a rearward end and a fiberoptic bundle extending forwardly within the endotracheal tube, and an adjustable positioning element through which the forwardly extending fiberoptic bundle passes for adjustably positioning and maintaining the tip end of the fiberoptic bundle relative to the forward end of the endotracheal tube. The apparatus is placed in the mouth, the larynx is identified and the endotracheal tube, housing and fiberoptic scope are advanced as a unit into the trachea as the blade is removed. Then the fiberoptic scope and housing are withdrawn, leaving the endotracheal tube in the desired part of the trachea. Some important objects of the fiberoptic intubating apparatus and method are the improvement of the difficult airway management, the minimization of the risk of airway trauma during the procedure of endotracheal intubation, the minimization of head and neck manipulation during laryngoscopy and intubation, the elimination of the need for stylets, forceps or other rigid instruments, the ability of continuous manipulation of the endotracheal tube in an unchanged fixed position within the field of view, and subsequent confirmation of placement of the tube in the desired part of the trachea, the achievement of a continuously illuminated field of view throughout the process of endotracheal intubation, the achievement of continuous protection of the field of view from obstruction by soft tissues, secretions or blood throughout the whole process of endotracheal intubation and the achievement of oxygen insufflation, suction application, and minimization of the risk of lethal aspiration during laryngoscopy and intubation.

14. Additional equipment and devices used for the management of a difficult airway includes (but is to limited to) endotracheal tube guides e.g. semirigid stylets with or without a hollow core for jet ventilation, light wands, forceps designed to manipulate the distal portion of the tube etc., devices suitable for emergency nonsurgical intubation e.g. the transtracheal jet ventilator, a hollow jet ventilation stylet, the laryngeal mask airway, the esophageal tracheal combitube etc., cricothyrotomy equipment and the exhaled $CO_2$ detector.

The advantages and disadvantages of the laryngeal mask airway when compared to the traditional technique of endotracheal intubation with the use of the standard Macintosh type or Miller type blades may be of particular interest:

Advantages

1. Less invasive
2. Less anesthetic depth required
3. Useful in difficult intubations
4. Less tooth and laryngeal trauma
5. Less laryngospasm and broncho-spasm
6. Muscle relaxation not required
7. Neck motility not required
8. Less elevation of intraocular pressure
9. Less risk of esophageal or endobronchial intubation
10. It is an effective alternative technique of ventilating a patient with a difficult airway in an emergency situation.

Disadvantages

1. Risk of gastrointestinal aspiration.
2. Prone or jackknife positions
3. Unsafe in morbidly obese
4. Limits maximum positive pressure ventilation
5. Less secure airway
6. Greater risk of gas leak and pollution.
7. Causes gastric distention.

The esophageal tracheal combitube provides a better seal and better airway protection against gastric aspiration than the laryngeal mask. However it is available only in one disposable adult size (age>15 years, height>155 cm) and is quite expensive. Its side perforations prevent its use as a guide for flexible fiberoptic bronchoscopy or intubation with a standard endotracheal tube. Its use is contraindicated in patients with an intact gag refer esophageal pathology, or a history of caustic substance ingestion.

15. From the great variety of alternative airway management techniques and methods reference should be made to the following techniques:

(i) The blind nasotracheal intubation. This technique has less prominent pathophysiologic effects (rigid laryngoscopy is avoided), but carries a higher risk of unintentional esophageal intubation and requires additional skill and experience as well.

(ii) The "awake intubation": The pathophysiologic consequences of this technique can be more prominent, because the patient's upper airway reflexes are totally or partially preserved. The administration of drugs such as lidocaine may attenuate the physiologic responses to airway instrumentation.

(iii) Tracheal intubation with the aid of a fiberoptic bronchoscope.

(iv) Retrograde intubation techniques.

16. Lastly the composition of algorithms such as the "A.S.A. difficult airway algorithm" provides useful guidelines for the selective or combined use of the various airway management techniques.

COMMENTS ON THE PRIOR ART a) General Comments

Despite the great variety of airway management devices, techniques and methods there are still significant unsolved problems including the possibility of airway trauma, and the control of the airway of patients with Cormack-Lehane grade IV laryngoscopic findings i.e. when it is impossible to visualize any anatomic structure of the larynx during "traditional" laryngoscopy.

Despite the great variety of airway management devices, techniques and methods there are still significant unsolved problems including the possibility of airway trauma, the control of the airway of patients with Cormack-Lehane grade IV laryngoscopic findings i.e. when it is impossible to visualize any anatomic structure of the larynx during "traditional" laryngoscopy with the standard Macintosh type curved blade, the pathophysiologic effects of airway instrumentation, and sometimes the complexity of the technique of endotracheal intubation which may require additional skill experience and time.

b) Particular Comments (i) Blind techniques increase the risk of esophageal intubation and of airway trauma through the use of stylets or obturators, and provide no visual evidence that the endotracheal tube has entered the trachea.

(ii) Direct laryngoscopy frequently requires head and neck positioning that may be either contraindicated or injurious to a patient with neck or head trauma. There is also a risk of inability to visualize any part of the larynx (Cormack-Lehane grade IV) and furthermore a risk of inability to intubate the trachea even if the larynx is identified. Also there is usually no means for oxygen insufflation or continuous suction application throughout the procedure of endotracheal intubation. Lastly the use of any rigid blade including the blade of the "levering laryngoscope" of Mccoy-Mirakhur) carries the risk of traumatizing the teeth, and any soft tissue (e.g. tongue, epiglottis) on which mechanical stress is exerted by the blade.

(iii) With rigid fiberoptic laryngoscopy the following disadvantages are still present:

(a) It may be difficult to intubate the trachea without rigid stylets or other guides which may damage the soft tissues of the upper airway.

(b) There is a risk of obstruction of the light source or field of view by the tube itself, blood, secretions or soft tissues.

(c) It may be impossible to confirm final tube position in the trachea.

(iv) With independent endoscope techniques such as the use of malleable fiberoptic stylets and flexible fiberoptic bronchoscopy it is impossible to retract tissues away from the pathway of the instrument and the endotracheal tube over it; the field of view is not continuously protected from blood, secretions or soft tissues and there is a risk of stylet produced injury. Furthermore it is difficult or impossible to use these types of instruments with just one hand.

(v) Lastly the use of the oral fiberoptic intubating apparatus and method (Flam and Gilbert U.S. Pat. No. 5,431,152) provides an alternative airway management technique applicable in both awake and unconscious patients. This technique probably facilitates difficult intubation, decreases the risk of upper airway trauma, avoids manipulation of head and neck throughout the process of intubation, allows confirmation of placement of the tube in the desired part of the trachea, provides a continuously illuminated and protected field of view throughout the process of endotracheal intubation, and allows oxygen insufflation and suction application throughout the process of endotracheal intubation.

The use of the oral fiberoptic intubating apparatus and method in airway management is related with the following problems:

(i) The need of direct manipulation of the smooth laryngeal surface of the epiglottis which comprises increased risk of both epiglottic trauma and of accentuation of the physiological responses to airway instrumentation.

(ii) The use of the fiberoptic scope requires additional skill and experience and furthermore the visualization of the larynx can only be indirect (i.e. through the eyepiece of the fiberoptic scope).

(iii) oxygen insufflation and suction application cannot be provided simultaneously.

(iv) Direct manipulation of the laryngeal surface of the epiglottis can be quite irritating in awake patients.

SUMMARY OF THE INVENTION

This invention relates to a new laryngoscope which is distinguished over the prior art in general by a flexible curved blade carrying two inflatable balloons, two thin double lumen tubes and one thin single lumen tube, operable means for insufflation of air into the balloons through the two thin double lumen tubes and for the change of the blade's contour as well are preferably provided at the handle of the laryngoscope. The distal two-thirds of the blade are connected to the proximal one-third through a joint. The angle between the axes of the proximal one-third and distal two-thirds of the blade can be varied at least between 200–100 degrees through operation of the joint.

Furthermore the distal two-thirds of the blade can move in many alternative directions (and not only in the direction of the handle) by operating the joint. As a corollary the use of the joint can significantly improve the field of viewing. The flexible blade is placed in the mount, its tip is advanced either up to the vallecula or under the laryngeal surface of the epiglottis and can be used for soft tissue displacement and exposure of the glottic opening alone or in combination with one (usually the right) or both balloons. The balloons (most frequently the right alone) can be used either alone or in combination with the flexible blade to expose the glottic opening.

The one lumen of either of the two thin double lumen tubes is used for the insufflation of air into the respective balloon, and the other lumen can be used either for oxygen insufflation or for suction application. As a corollary suction application and oxygen insufflation can be simultaneous throughout the procedure of laryngoscopy and intubation.

The thin single lumen tube which lies between the two thin double lumen tubes has the following characteristics:

(i) Its rearward (proximal end) is located on the proximal quarter of the blade's concave surface and its tip extends only 1–2 mm distally to the tip of the blade.

(ii) It is made of suitable material in order to be compliant enough so that a thin bundle of optic fibers can be passed through it. This additional ability of "flexible" fiberoptic laryngoscopy eliminates the need of head and neck manipulation throughout the process of endotracheal intubation.

OBJECTS OF THE INVENTION

It is therefore an object of the present invention to provide a new laryngoscope with a flexible blade, two inflatable balloons, two thin double lumen tubes and one thin single lumen tube, which can be sued to facilitate rapid, successful and nonlethal oral endotracheal intubation of both unconscious and awake patients.

It is another object of this invention to provide a new laryngoscope and new laryngoscopic techniques which reduce the risk of upper airway trauma throughout the process of endotracheal intubation.

Another object of this invention is to provide a new alternative "flexible" fiberoptic laryngoscopic technique which allows minimal mouth opening and minimal manipulation of the head and neck throughout the process of endotracheal intubation.

Another object of this invention is to provide new techniques of exposure of the glottic opening through balloon inflation in order to:

(i) facilitate difficult airway management (ii) decrease the risk of traumatizing the epiglottis, especially in patients with difficult intubation, (iii) attenuate the physiological responses to airway instrumentation.

Another object of this invention is to provide a new laryngoscope with a flexible blade which can be used alone or in combination with one or two inflatable balloons to expose the glottic opening without any movement of the handle and without any head and neck manipulation.

Another object of this invention is to provide a new laryngoscope which allows simultaneous oxygen insufflation and suction application throughout the process of endotracheal intubation.

GENERAL DESCRIPTION OF THE INVENTION

The above noted objects and other objects of the invention are accomplished by a laryngoscope with a flexible blade which has a joint incorporated at the distal end of its proximal one third. This joint when operated allows increase or decrease of the angulation of the blade's distal two-thirds in relation to its proximal one-third. The change in the angulation of the blade's distal two-thirds can take place in many alternative directions and not only in the direction of the handle.

The flexible blade also carries two thin double lumen tubes and one thin single lumen tube. The two thin double lumen tubes are placed on the right and left edge of the blade and extend longitudinally from the proximal to the distal end of the blade. The one lumen of each double lumen tube is used to inflate a respective balloon which is incorporated at the distal quarter of each thin double lumen tube. The proximal part of the connected to the balloon one lumen of each thin double lumen tube extends into the handle and terminates at a mechanism of air insufflation control, which is incorporated at the proximal part of the handle so that the corresponding to it control know of air insufflation is located close to the index finger of an operator, who grasps the handle in order to perform laryngoscopy.

The other lumen of each thin double lumen tube has a free proximal part and end which extends proximally to the proximal end of the blade and can be placed in a short tubular housing located at the distal part of the handle, 2–3 centimeters above the part of the handle to which the proximal part of the blade is removably attached. The thin single lumen tube is placed on the blade's concave surface in between the two thin double lumen tubes, and extends longitudinally from the tip of the blade up to its proximal quarter. This compliant and transparent tube can house a thin fiberoptic bundle which can be inserted through its proximal end and advanced through its distal end under the laryngeal surface of the epiglottis, to facilitate both identification of the glottic opening and maneuvering of the tip of an endotracheal tube in order to achieve successful insertion of the tube into the trachea. The use of the fiberoptic bundle offers independent additional indirect visualization of the area of interest i.e. the glottic opening and of the relative position of the endotracheal tube's tip during the most critical part of the process of endotracheal intubation i.e. during the insertion attempt of the tip of the endotracheal tube in the glottic opening. As a corollary more accurate and less traumatic maneuvering of the tip of the endotracheal tube is achieved especially patients with difficult airways. Lastly the fiberoptic bundle can be used to confirm correct tube placement in the trachea.

The tips of the two thin double lumen tubes and of the thin single lumen tube extend only 1–2 millimeters distally to the flexible blade's tip.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
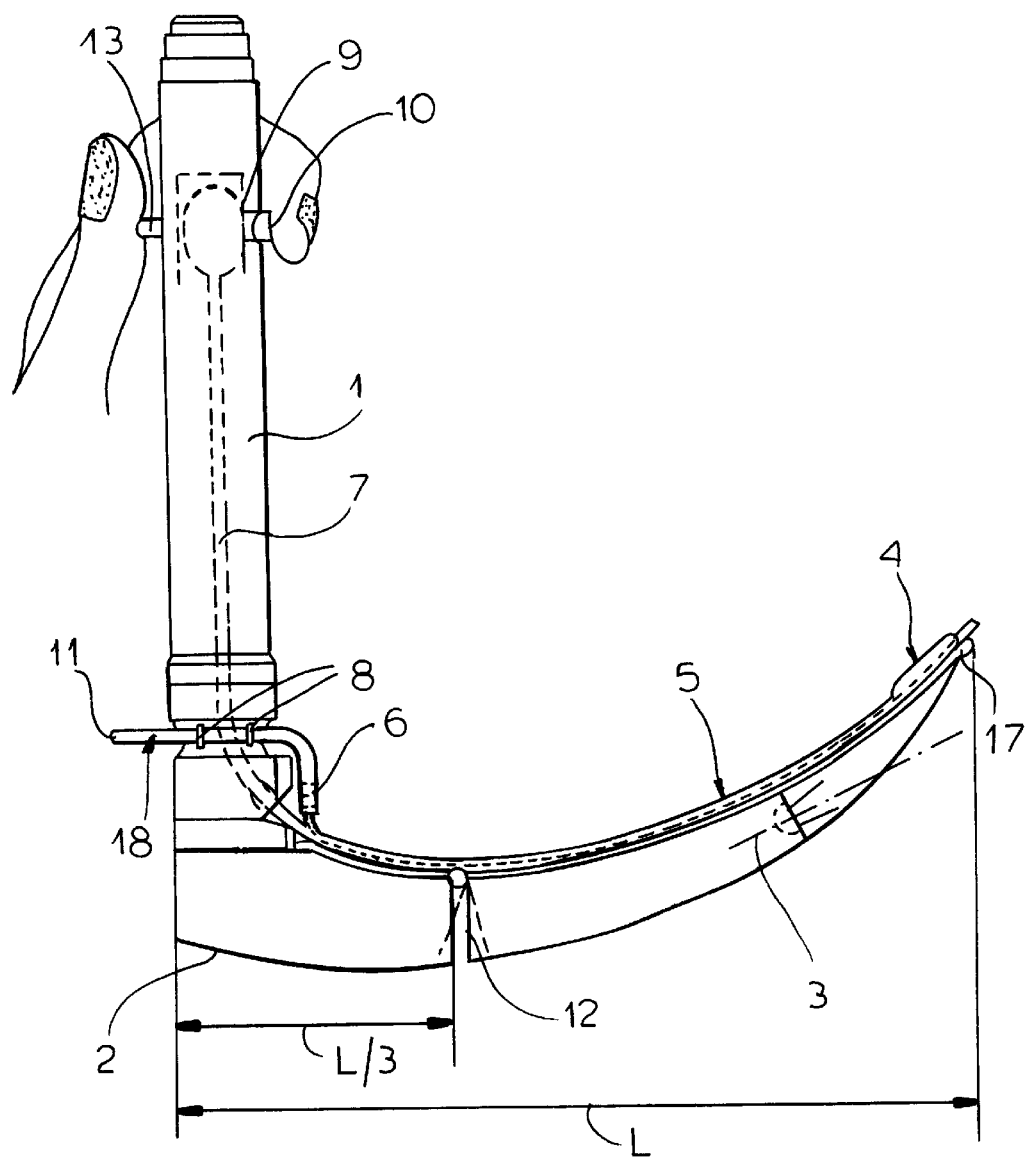
FIG. 1 is a side elevational view of the laryngoscope of the invention illustrating portions of the blade actuating mechanism and the balloon inflating mechanism in diagrammatic form.

FIG. 1 is a side view of the new laryngoscope showing the handle 1, blade 2, light source 3, the location of a deflated balloon 4, a thin double lumen tube 5, the connection points 6 between the proximal ends of each lumen of the thin double lumen tube and their respective tubular extensions 7 in the handle and in the tubular housing of the handle 8, the mechanism 9 for insufflation of air into a balloon and the approximate location of its respective control knob 10, the rearward end 11 of the extension of the second lumen of a thin double lumen tube for oxygen insufflation or suction, the joint 12 and its respective control lever 13.

Figure 2:
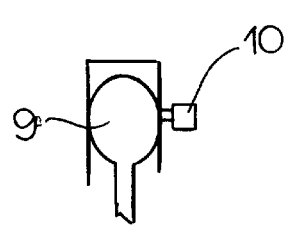
FIG. 2 is a detail of the balloon inflating mechanism.
Figure 4:
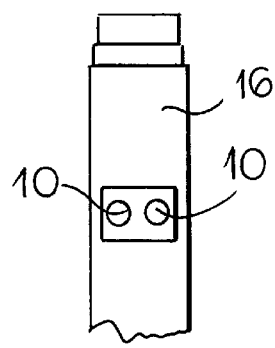
FIG. 4 is a partial front view of the handle showing two buttons for inflating the two balloons.
Figure 3:
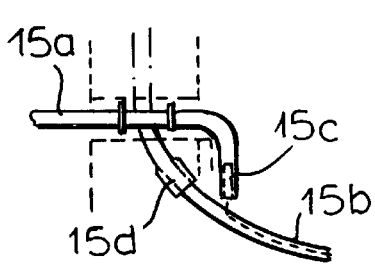
FIG. 3 is a detail of the connections to the lumens at the end of the blade connected to the handle.

FIG. 2 shows the principle of the mechanism of air insufflation into a balloon and FIG. 3 shows the tubular housing 8 of the handle and the connection points 15c, 15d between the proximal ends of the two tubes of a thin double lumen tube and the distal ends of their respective tubular extensions e.g. 15a at the handle. FIG. 4 shows a frontal aspect 16 of the proximal part of the handle with the two control knobs for air insufflation into the flexible blade's balloons. The tip of the flexible blade is shown at 17. A thin single lumen tubular extension for oxygen insufflation or suction application is shown at 18.

Figure 7:
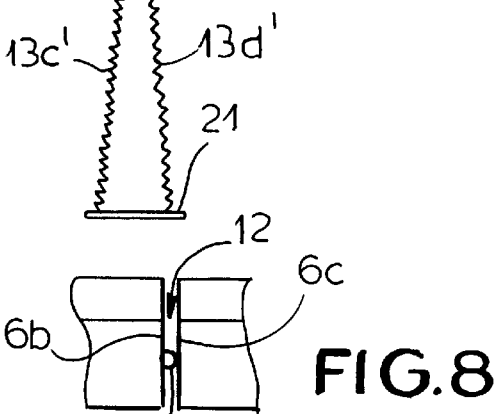
FIG. 7 is a diagram illustrating the blade articulation mechanism.
Figure 6:
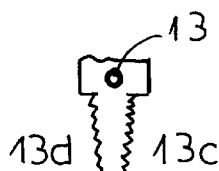
FIG. 6 is a partial rear view of the handle showing the actuator for the blade articulation mechanism.
Figure 8:
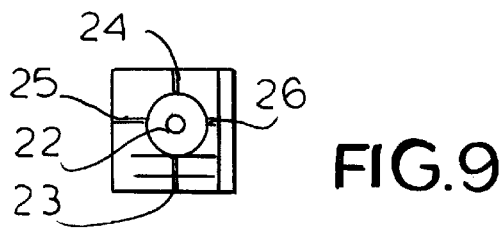
FIG. 8 is a detail of the hinge or articulation.
Figure 9:
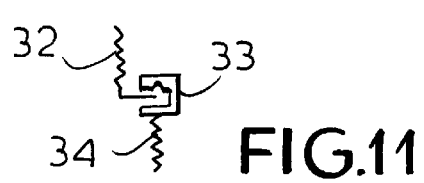
FIG. 9 is a detail of the distal end of the handle.
Figure 5:
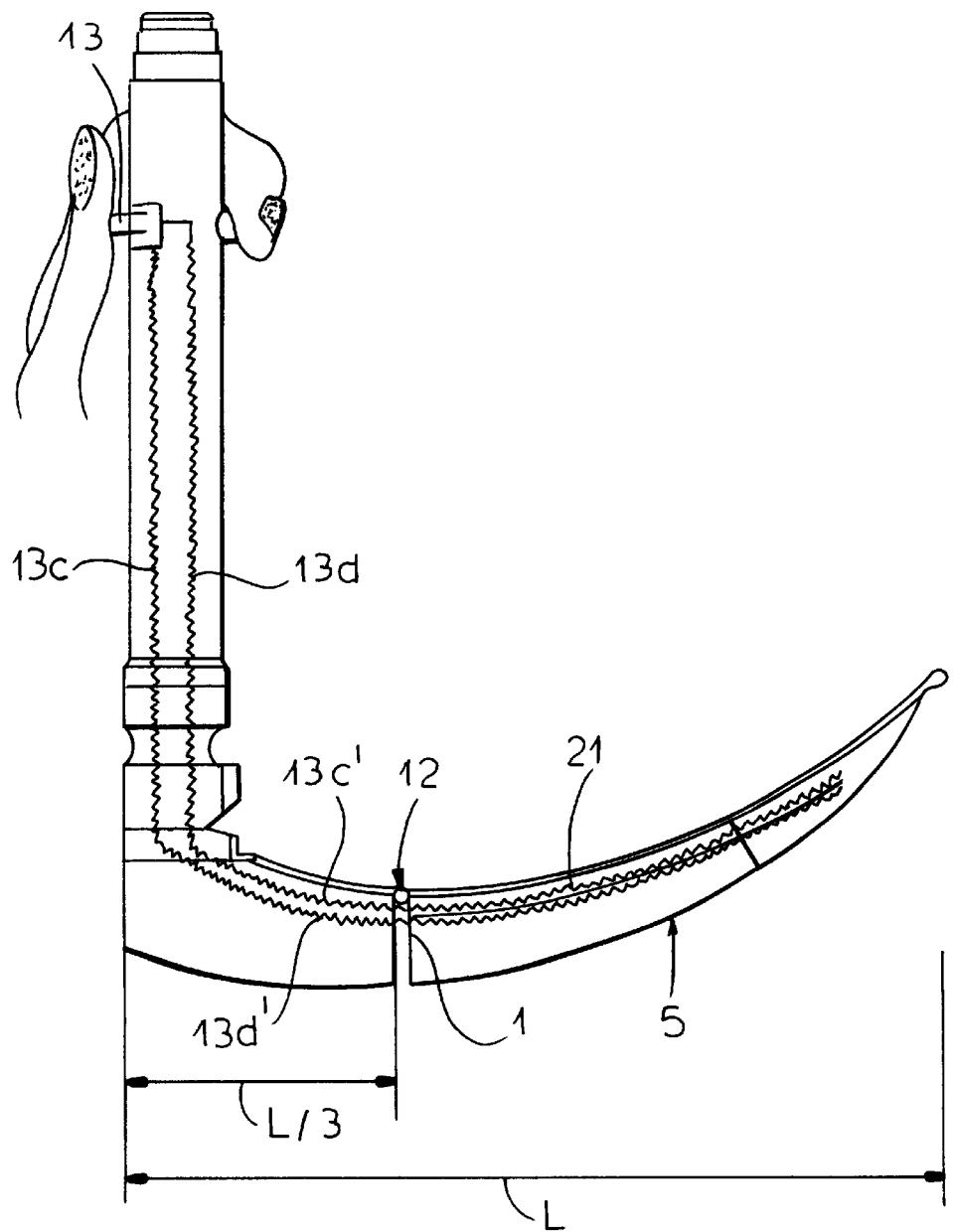
FIG. 5 is another side elevational view of the laryngoscope from which the balloons, tubes and balloon inflators have been omitted and diagrazmatically illustrating the mechanism for effecting increased or decreased angulation of the articulated blade portion.

FIG. 5 is a side view of the new laryngoscope showing details of the joint 12 and some details of its control mechanism. For simplicity and more effective description the thin single lumen tube, the thin double lumen tubes, balloons, mechanisms of air insufflation and respective control knobs are omitted. The joint 12 controlled by lever 13 is formed by a plate 21 incorporated in the distal two-thirds of the blade. FIG. 6 a rearward view of the proximal part of the handle where the joint's control lever 13 is located. FIG. 7 is a frontal section of the handle and a mechanism for the plate's (and consequently of the blade's distal two thirds) rotation. The frontal section of the joint's control lever 13 acts via springs 13c, 13c contained in the handle and springs 13c', 13d' incorporated in the flexible blade. FIG. 8 shows a preferable version of the joint, which consists of one sphere, 6a, one proximal contact surface 6b and one distal contact surface 6c. FIG. 9 shows the distal end of the handle in which the proximal end of the blade is removably attached and slidably engaged. The contact area for the conduction of electricity to the blade's light source is shown at 22. The section of the extension of the spring responsible for the increase in the blade's distal two-thirds angulation is shown at 23. The section of the extension of the spring responsible for the decrease in the blade's distal two-thirds angulation is seen at 24.

The sections of the extensions of the two springs responsible for the rotation of the blade's distal two-thirds are shown at 25 and 26.

Figure 10:
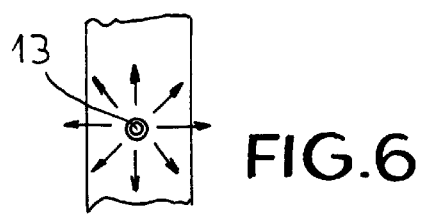
FIG. 10 is another detail of the handle structure.

FIG. 10 shows the proximal part of the blade, which is removably attached and slidably engaged in the distal part of the handle. The contact area for the conduction of electricity to the blade's light source is shown at 27. The section of the extension of the spring responsible for the increase in the blade's distal two-thirds angulation is seen at 28. The section of the extension of the spring responsible for the decrease in the blade's distal two-thirds angulation is represented at 29. The sections of the extensions of the two springs responsible for the rotation of the blade's distal two-thirds are shown at 30, 31.

Figure 11:
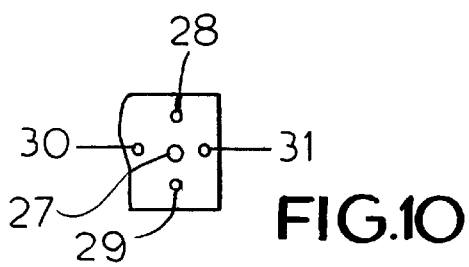
FIG. 11 is a detail showing the spring attachments.

FIG. 11 shows one of several alternative mechanisms for firm attachment between the springs' extensions. A spring extension from the handle is seen at 32. A small metallic cube with a small central tube in which the distal part of 32 can be slidably engaged in seen at 33. A spring extension from the blade with a proximal end incorporated in cube 32 is seen at 34.

Figure 12:
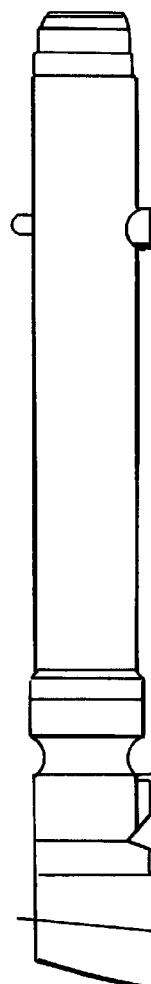
FIG. 12 is a side elevational view of the laryngoscope illustrating the function of the joints;'
Figure 13:
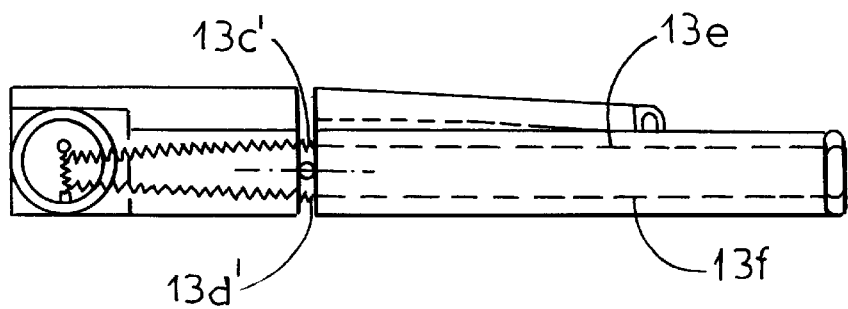
FIG. 13 is a top view of the laryngoscope.

FIGS. 12 and 13 show the operation of the joint 12. The increased angulation of the flexible blade is depicted at 35 with an intermediate angulation of the flexible blade seen at 36 and a limited angulation of the flexible blade at 37. FIG. 13 shows a view from above when the distal two-thirds of the blade are rotated by operating the joint 12 by the springs 13c', 13d' responsible for rotation giving leftward rotation 13e or rightward rotation 13f.

The two thin double lumen tubes, the inflatable balloons and the one thin single lumen tube are omitted for simplicity of description. The area of the joint is covered by smooth elastic material so that there are no sharp metallic protrusions.

Figure 14:
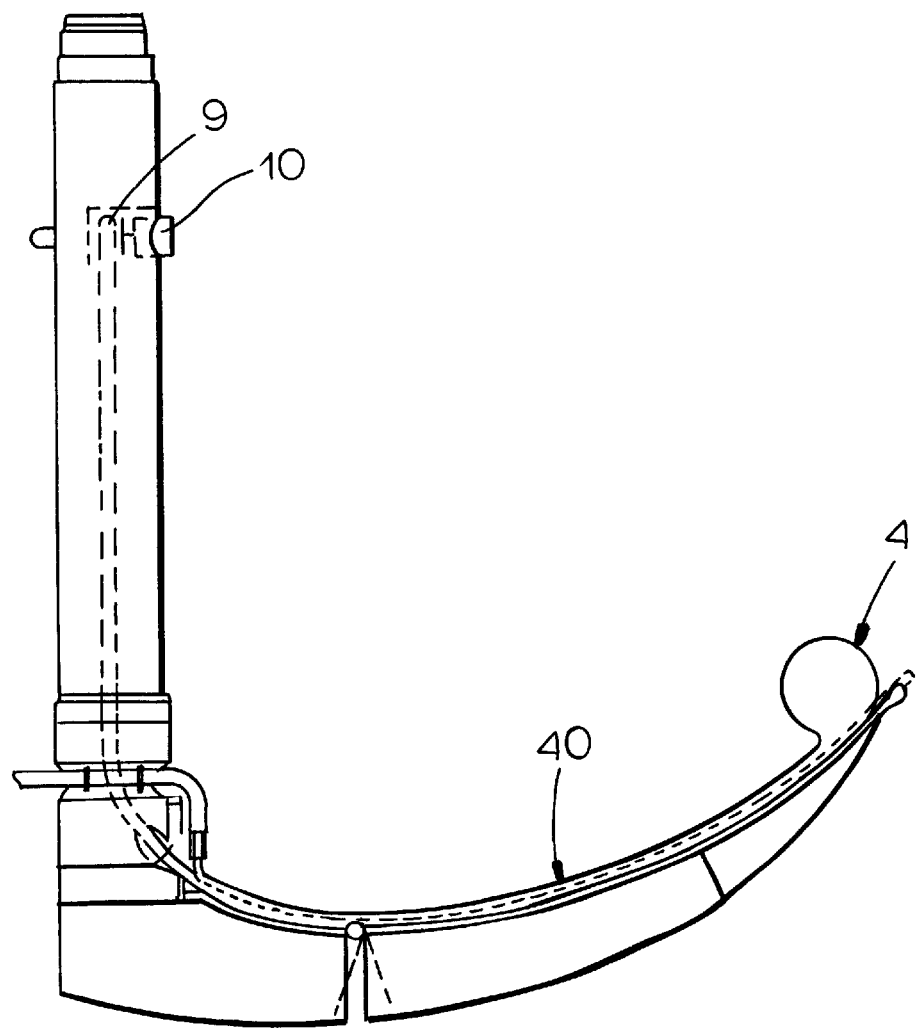
FIG. 14 is a side elevation of the laryngoscope with the angulation mechanism being omitted and the tubes and balloons shown in detail.
Figure 15:
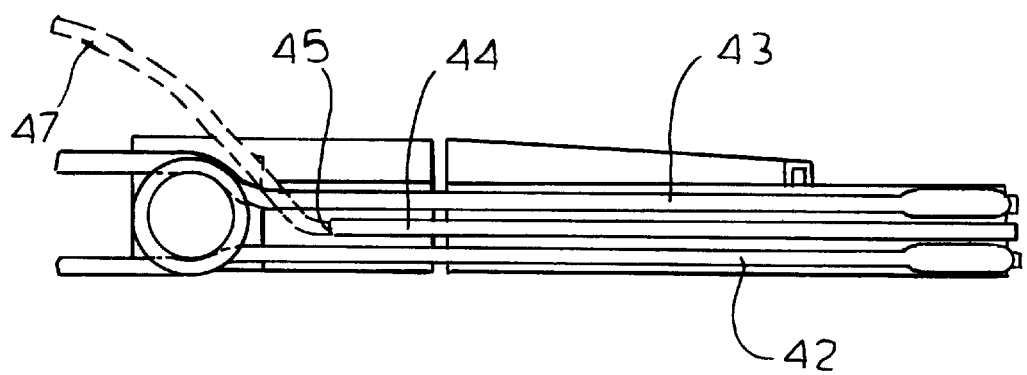
FIGS. 15, 16 and 17 are diagrams illustrating the tube and balloon configurations.
Figure 16:
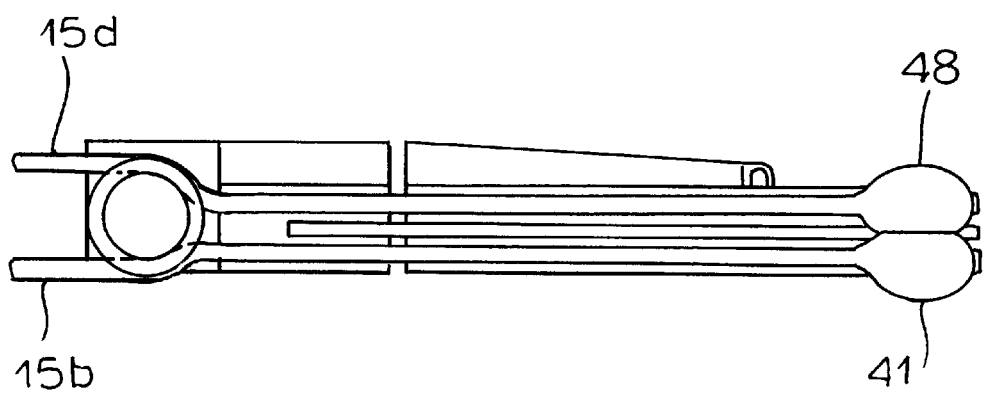

FIGS. 14–17 show details of the balloons and the tubes. FIG. 14 shows the right thin double lumen tube 49 and the inflated right balloon 41. The more compliant pilot balloon 9 has been compressed by the corresponding control knob 10. FIG. 15 shows in a view from above the right thin double lumen tube 42, the left thin double lumen tube 43, the thin single lumen tube 44, the proximal end of thin single lumen tube 45, the distal end of thin single lumen tube 46 and the fiberoptic bundle 47. FIG. 16 shows a view from above with both balloons 41, 48 inflated. The proximal free ends of the extensions are represented at 15b, 15d.

Figure 17:
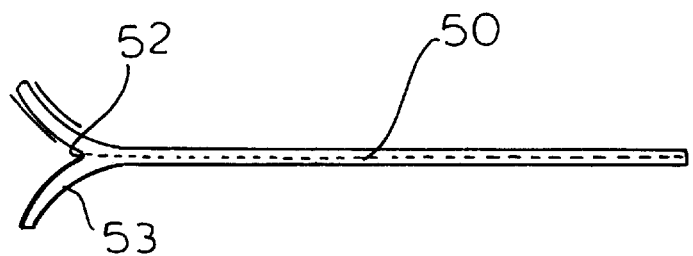

FIG. 17 shows a larger view of a thin double lumen tube 42 or 43. In such a tube, the first lumen for air insufflation into the deflated balloon can be seen at 50, the second lumen for continuous oxygen insufflation or suction application at 51, the connection point at 52 and the proximal free end (available for connection) of the second lumen at 53.

If there is no contraindication the patient's neck can be flexed and his (or her) head can be extended in order to achieve alignment of the oral, pharyngeal and laryngeal axes just prior to laryngoscopy.

After opening the patient's mouth the flexible blade 5 is inserted into the right side of the oropharynx, the tongue is displaced to the left and up into the floor of the pharynx by the flexible blade's flange and the flexible blade's tip 17 is inserted into the vallecula.

Now the doctor performing laryngoscopy has the following alternative laryngoscopic and intubating manoeuvres at his disposal.

a) He can gradually inflate the right balloon 41 by applying gradually increasing pressure on the corresponding control knob with his left or right index finger until adequate exposure of the glottis for intubation is achieved.

The right balloon 41 when gradually inflated causes a smooth upward displacement of the soft tissues of the vallecula with minimal mechanical stress and a subsequent elevation of the epiglottis and frequently adequate (for endotracheal tube insertion) exposure of the glottic opening.

b) If right balloon inflation 41 does not achieve the desired exposure of the glottic opening the operator can increase the angulation of the flexible blade by activating the joint 12 through the use of the corresponding control lever 13 in order to cause further elevation of the epiglottis and greater exposure of the glottis.

If the patient's larynx (and consequently the glottis) is displaced either to the left or to the right by a disease process or trauma the operator can (either before or after the increase in the angulation 35 of the flexible blade 5 rotate the distal two-thirds of the blade 5 towards the direction of the laryngeal displacement by moving the control lever horizontally and in the opposite direction of the laryngeal displacement with his thumb. The horizontal movement of the control lever will activate the joint's rotation mechanism 13c, 13d.

c) If the combined balloon inflation and joint activation cannot cause sufficient exposure of the glottis the operator can still raise the handle up and away from the patient in a plane perpendicular to the patient's mandible in order to achieve adequate glottic visualization for endotracheal tube insertion.

d) If the combination of the previous manoeuvres does not provide sufficient exposure of the glottis, the operator (or an assistant) can insert a thin fiberoptic bundle through the proximal end of the transparent thin single lumen tube and advance it through its distal end, and under the laryngeal surface of the already elevated by previous right balloon inflation epiglottis. The larynx will be identified through the eyepiece of the fiberoptic bundle and additionally the relevant position of the flexible blade's tip to the glottic opening will be known so that any further manoeuvre (such as further change in the blade's angulation or further right balloon inflation or slight right balloon deflation or left balloon inflation) will be more efficient in achieving adequate direct exposure of the glottis and subsequent tube insertion.

e) If the glottis can be identified only indirectly (i.e. through the eyepiece of the thin fiberoptic bundle 47) the endotracheal tube can be inserted into the mouth or through a nostril and advanced towards the tip of the fiberoptic bundle. The tube's tip will be successfully and rapidly manoeuvred into the glottic opening as soon as it becomes visible through the eyepiece of the fiberoptic bundle so that its relevant position to the glottic opening will be known.

Alternatively if manipulation of head and neck are contraindicated the operator can apply the following technique.

a') Decrease of the flexible blade's angulation through operation of the joint.

b') Insertion of a thin fiberoptic bundle into the thin single lumen tube through its proximal end. The top of the thin fiberoptic bundle is advanced just proximally to the tip of the thin and transparent single lumen tube.

c') The flexible blade is then inserted into the right side of the patient's mouth and its tip is advanced under the laryngeal surface of the epiglottis under indirect vision through the eyepiece of the already incorporated (step b) fiberoptic bundle.

d') The epiglottis is then displaced smoothly and without any risk of trauma through inflation of the right balloon. If additional direct vision of the glottic opening is achieved the operator inserts an endotracheal tube into the patient's trachea.

e') After inflation of the balloon the operator can increase the initially decreased angulation of the flexible blade by reactivating the joint. If adequate direct vision of the glottis is achieved, the operator intubates the patient's trachea.

f') The field of direct visualization can still be extended (after steps a', b', c', d', e' have already been followed) by raising the handle of the laryngoscope up and away from the patient in a plane perpendicular to this (or her) mandible.

g') If the glottic opening cannot be directly identified after steps a', b', c', d', e' f' the operator can advance the thin fiberoptic bundle through the distal end of the single lumen tube, identify the glottis, insert the endotracheal tube into the oropharynx (through the patient's mouth or through one of the patient's nostrils), direct the tube's tip towards the top of the thin fiberoptic bundle and insert the tube's tip through the glottic opening under indirect vision through the thin fiberoptic bundle's eyepiece. The thin fiberoptic bundle can then be advanced along with the endotracheal tube into the trachea to confirm correct tube placement.

Additionally the operator has the option of continuous and simultaneous suction application and oxygen insufflation through the free proximal end of each second lumen of each of the two thin double lumen tubes, throughout the process of laryngoscopy and intubation. Additionally the operator has the option of rotating the distal two-thirds of the flexible blade through activation of the corresponding mechanism by moving the lever horizontally with his thumb, in order to achieve better exposure of a due to trauma, or disease process displaced glottis.

Advantages

The new laryngoscope with a flexible blade, two inflatable balloons, two thin double lumen tubes and one thin single lumen tube offers the following important advantages:

1. Facilitation of the difficult airway management.

The combined use of the joint and the balloons (the right balloon is most frequently used alone) offers new techniques of extending the field of visualization and of exposing the glottis. Consequently it will be easier to intubate patients with conditions associated with a narrow field of visualization (e.g. prominent upper incisors, inadequate mouth opening), or with inability of alignment of the oral, pharyngeal and laryngeal axes (e.g. anterior larynx, ankylosing spondylitis).

Furthermore in conditions associated with contraindication of head and neck manipulation (e.g. cervical spine injury) the visualization of the glottis can be achieved through the eyepiece of the thin fiberoptic bundle after the flexible blade with decreased angulation has been placed under the laryngeal surface of the epiglottis and the inflated right balloon has smoothly and sufficiently displaced the epiglottis in order to create a relatively wide passage for the tip of the thin fiberoptic bundle. This latter technique greatly facilitates airway management in traumatized patients whose otherwise frequently easy intubation can become difficult because of the contraindication of head and neck manipulation.

2. Continuous and simultaneous oxygen insufflation and suction application through the proximal ends of the two "second lumens" of the two thin double lumen tubes. This technique decreases the risk of fatal hypoemia during laryngoscopy and intubation and allows simultaneous removal of blood and secretions from the field of visualization. As a corollary the procedure of endotracheal intubation becomes both safer and faster.

3. Less risk of airway trauma: the flexible blade provides alternative ways of extension of the field of visualization such as increased angulation and rotation of its distal two-thirds: leverage on the upper teeth is easily avoided and the mechanical stress on the soft tissues is minimized, because the change in the blade's contour through the operation of its joint provides maximal extension of the field of visualization with the least possible mechanical deformation of the upper airway's soft tissues, which must be displaced in order to achieve glottic exposure, by approximating their initial curvature (i.e. their curvature just prior to laryngoscopy). The displacement of the susceptible to trauma tissues of the vallecula (and the subsequent elevation of the epiglottis) is achieved through the inflation of the balloons (most frequently only the right balloon is inflated), which have a very smooth surface that virtually eliminates the risk of lacerations.

Additionally when the flexible blade's angulation is decreased and its tip is placed under the more susceptible to trauma than the tissues of the vallecula laryngeal surface of the epiglottis (under indirect visualization through the eyepiece of the fiberoptic bundle) the direct displacement of the epiglottis through balloon inflation virtually guarantees its mechanical integrity.

4. Less prominent physiologic responses to airway instrumentation.

The irritant receptors which lie between airway epithelia cells and respond to noxious stimuli (including mechanical stress) seem to play an important role in the generation of the physiologic responses to airway instrumentation. These receptors show rapid adaptation to mechanical stimulation i.e. the deformation of the nerve terminal they contain is not maintained during continuous stimulus application. Furthermore usually only rapidly applied (or sufficiently forceful) stimuli such as pressure exertion by a metallic blade can generate an action potential in the contained nerve terminal and the intensity of the resulting physiologic responses (elevation of arterial, intracranial and intravascular pressure and increased heart rate) to airway instrumentation is directly proportional to the number of irritant receptors which are effectively deformed when pressed by a rigid metallic blade.

The gradual and smooth soft tissue displacement by balloon inflation decreases the individual probability of effective deformation of each mutant receptor contained in the area of displaced soft tissues. As a corollary the effective stimulation of a smaller number of irritant receptors will result in less intense physiologic responses. This advantage can be of particular value in patients with coronary artery disease who cannot tolerate acute increases in myocardial oxygen consumption due to acute elevations of systolic arterial pressure and sudden increases in heart rate, and in patients with head traumas, who cannot tolerate further acute elevations of an already elevated intracranial pressure.

What is claimed is:

1. A laryngoscope for tracheal intubation which comprises in combination:
   a flexible elongated blade comprising in combination:
   (i) a joint which allows both gradual increase and gradual decrease in angulation of a distal two thirds of said blade in combination with either leftward or rightward rotation of said blade, so that the contour of said blade can be changed in many directions, and not only in the direction of the handle, according to the operator's clinical decision,
   (ii) a system of four springs and a spatulated plate serving in combination with the joint as part of a mechanism responsible for the changes of flexible blade contour,
   (iii) two thin double lumen tubes each carrying an inflatable balloon at a distal quarter,
   (iv) one thin single lumen tube on a concave surface of said blade in between said two thin double lumen tubes; and
   a handle comprising in combination
   (i) two control knobs, two pilot balloons and two thin single lumen tubes for independent inflation of each said inflatable balloons,
   (ii) a control lever and a system of four springs as operable means for the changes in the said flexible blade's contour, and
   (iii) two tubular housings each of which is attached to one of the two lateral exterior surfaces of a distal one-fifth of said handle, and each of which contains one thin single lumen tube.

2. The laryngoscope of claim 1 in which said joint is incorporated at a distal part of said flexible blade's proximal one-third.

3. The laryngoscope of claim 1 in which the joint does not cause any sharp protrusions to the contour of said flexible blade.

4. The laryngoscope of claim 1 in which each of said four springs which are incorporated in said flexible blade has a proximal end extending approximately 2 mm proximally to the proximal end of said flexible blade and is incorporated into a small receptor mechanism.

5. The laryngoscope of claim 4 in which each of the distal ends of said four springs of said handle extends approximately 2–3 mm distally to the distal surface of said handle and is always slidably engaged into the corresponding said receptor mechanism of the corresponding said spring of said flexible blade, when the proximal end of said flexible blade is slidably engaged in the distal end of said handle.

6. The laryngoscope of claim 5 in which two of said four springs of said handle serve as part of the mechanism for leftward and rightward rotation of the distal two-thirds of said flexible blade and their distal ends can be removably attached and slidably engaged into the proximal receptor mechanisms of the proximal ends of the corresponding said two springs of said flexible blade.

7. The laryngoscope of claim 5 in which one of four said springs of said handle serves as part of the mechanism responsible for the increase in the angulation of said flexible blade, and its distal end can be removably attached and slidably engaged into the proximal receptor mechanism of the corresponding said one spring of said flexible blade.

8. The laryngoscope of claim 5 in which one of four said springs of said handle serves as part of the mechanism for the decrease in the angulation of said flexible blade, and its distal end can be removably attached and slidably engaged into the proximal receptor mechanism of the corresponding said one spring of said flexible blade.

9. The laryngoscope of claim 5 in which a lever movable in all directions preferably by the operator's thumb is provided at the rearward surface of the proximal part of said handle along with means for stretching each of four said springs of said handle installed firmly within the hollow core of the proximal part of said handle.

10. The laryngoscope of claim 5 in which two said thin double-lumen tubes of said flexible blade extend longitudinally along the concave surface of said flexible blade, each having a distal end extending 1–2 mm distally to the tip of said flexible blade.

11. The laryngoscope of claim 10 in which each of said thin double-lumen tubes has one lumen (called first lumen)

serving for either oxygen insufflation or suction application throughout the process of laryngoscopy and endotracheal intubation.

12. The laryngoscope of claim 10 in which each of said thin double-lumen tubes of said flexible blade has two proximal free ends each corresponding to one of its lumens and each is available for connection with the distal end of a corresponding to its thin single-lumen tube of said handle.

13. The laryngoscope of claim 10 in which said handle contains two thin single-lumen tubes each extending longitudinally along the internal surface of each of the two lateral aspects of said handle, and each having a proximal end incorporated into a pilot balloon and a distal end available for connection with the proximal end of the corresponding to its first lumen of the unilateral thin double-lumen tube.

14. The laryngoscope of claim 10 in which each said pilot balloons is located in the proximal one-third of said handle and is at least three times more compliant than the corresponding inflatable balloon of said blade.

15. The laryngoscope of claim 10 in which each said thin single-lumen tubes contained in each said tubular housing of said handle has a distal end available for connection with the proximal end of the second lumen of the corresponding thin double-lumen tube of said handle and a distal free end available for either oxygen insufflation or suction application.

16. The laryngoscope of claim 5 in which said thin single-lumen tube of said flexible blade extends longitudinally along the medial part of the concave surface of said blade and has a distal end extending 1–2 mm distally to the tip of said flexible blade, and a proximal end located on the proximal quarter of said flexible blade.

17. The laryngoscope of claim 16 in which said thin single-lumen tube of said flexible blade has a high specific compliance which allows both easy insertion and advance of a thin fiberoptic bundle through its proximal end and lumen, respectively.

18. The laryngoscope of claim 5 in which said thin single-lumen tube of said flexible blade is made of transparent material.

19. The laryngoscope of claim 5 in which said thin double-lumen tubes and said thin single-lumen tube do not cause any limitation to the extent of clinically-desired changes in said flexible blade's contour.

20. The laryngoscope of claim 5 in which corresponding to the area of said joint external structures of said thin double-lumen tubes and of said thin single-lumen tube are suitably reinforced so that no obstruction to any lumen of any of said tubes of said flexible blade can be caused by any clinically-desired change in said flexible blade's contour.

21. The laryngoscope of claim 1 in which said spatulated plate is incorporated in the distal two-thirds of said flexible blade and has a shape similar to the shape of the distal two-thirds of said flexible blade and one concave and one convex surface with length and width slightly smaller than the length and width of the respective concave and convex surfaces of said flexible blade.

22. The laryngoscope of claim 1 in which said spatulated plate of said flexible blade has a proximal end located at the proximal end of said distal two-thirds of said flexible blade.

23. The laryngoscope of claim 1 in which the two of said four springs of said flexible blade serve for the leftward and rightward rotation of the distal two-thirds of said flexible blade and their distal ends are firmly attached to the proximal end of said spatulated plate.

24. The laryngoscope of claim 1 in which one of said four springs of said flexible blade serves to increase the angulation of the distal two-thirds of said flexible blade and is firmly attached to the concave surface of said spatulated plate extending up to the tip of said spatulated plate.

25. The laryngoscope of claim 1 in which one of said four springs of said flexible blade serves to decrease the angulation of the distal two thirds of said flexible blade and is firmly attached to the convex surface of said spatulated plate extending up to the tip of said spatulated plate.

* * * * *